US009146183B2

(12) United States Patent  (10) Patent No.: US 9,146,183 B2
O'Rourke  (45) Date of Patent: Sep. 29, 2015

(54) SELF-ALIGNING TEST WEIGHT

(71) Applicant: Jeffrey O'Rourke, Appomattox, VA (US)

(72) Inventor: Jeffrey O'Rourke, Appomattox, VA (US)

(73) Assignee: Jeffrey O'Rourke, Appomattox, VA (US)

( * ) Notice: Subject to any disclaimer, the term of this patent is extended or adjusted under 35 U.S.C. 154(b) by 219 days.

(21) Appl. No.: 13/915,314

(22) Filed: Jun. 11, 2013

(65) Prior Publication Data

US 2013/0327153 A1   Dec. 12, 2013

Related U.S. Application Data

(60) Provisional application No. 61/658,216, filed on Jun. 11, 2012.

(51) Int. Cl.
*G01N 3/02* (2006.01)
*B66C 15/00* (2006.01)
*G01G 19/14* (2006.01)

(52) U.S. Cl.
CPC  *G01N 3/02* (2013.01); *B66C 15/00* (2013.01); *G01G 19/14* (2013.01)

(58) Field of Classification Search
CPC ......... G01N 3/02; G01G 21/26; G01G 21/28; B66C 1/40; B66C 15/00; B66C 15/02; B66C 1/16; B66C 3/00; B66C 23/52; B66C 23/72; B66C 23/74; B66C 23/76; B66C 2700/0392
USPC ........................................................ 73/826
See application file for complete search history.

(56) References Cited

U.S. PATENT DOCUMENTS

| | | | |
|---|---|---|---|
| 5,445,032 A * | 8/1995 | Dixon ............................ 73/788 |
| 5,987,840 A | 11/1999 | Leppert | |
| 6,578,441 B1 | 6/2003 | Jurenka et al. | |
| 6,725,730 B2 | 4/2004 | Bollinger, Jr. | |
| 7,871,357 B2 * | 1/2011 | Gibson et al. .................... 482/98 |
| 2003/0037623 A1* | 2/2003 | Bollinger, Jr. ............ 73/862.392 |
| 2006/0130712 A1* | 6/2006 | Wang ........................... 108/57.25 |
| 2010/0224583 A1* | 9/2010 | Mentink et al. ................ 212/175 |
| 2014/0000968 A1* | 1/2014 | Yustus ............................... 177/1 |

* cited by examiner

*Primary Examiner* — Lisa Caputo
*Assistant Examiner* — Philip Cotey
(74) *Attorney, Agent, or Firm* — New River Valley IP Law, PC; Michael L. Mayberry

(57) ABSTRACT

The present invention relates to test weights for testing the load capacity of a crane. More specifically, the present invention provides a novel system and approach simple and efficient crane load testing using solid weights. Previous methods of testing crane load capacity often require significant time to configure and reconfigure the apparatus. The system of the present invention increases efficiency by significantly reducing this configuration time. The system comprises a plurality of stackable test weights, and a lifting fixture specifically designed for the system. A cantilever structure located on two opposing sides of the test weight enables the lifting fixture to first be quickly secured underneath of said structure, and then lift that particular unit as well as any units surmounting that unit. A novel block lock system integrated into each weight unit enables self-alignment and securing of each weight as it is placed onto the weight stack.

20 Claims, 9 Drawing Sheets

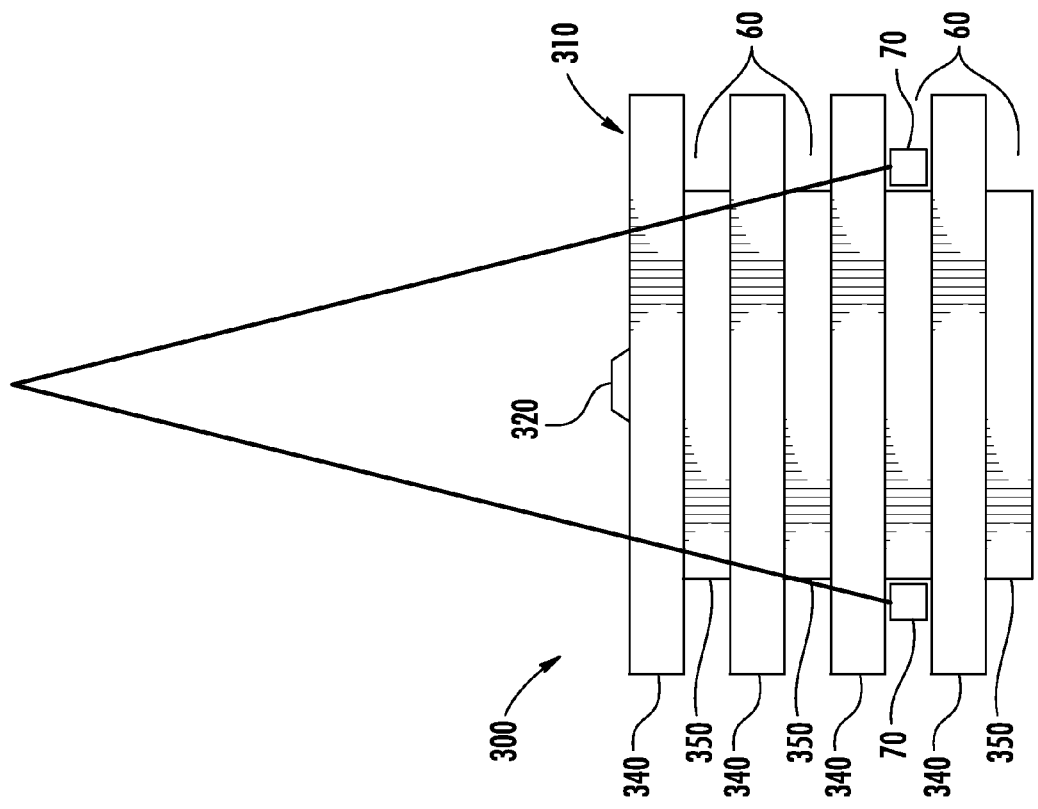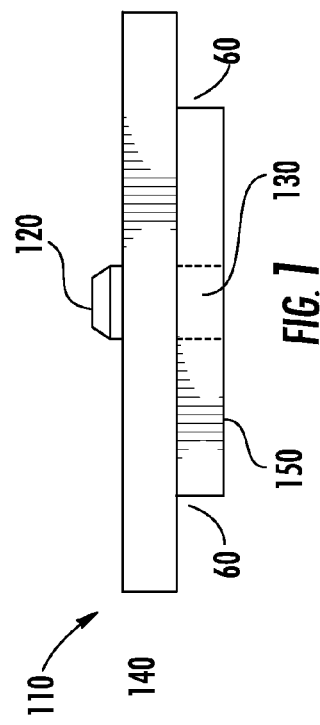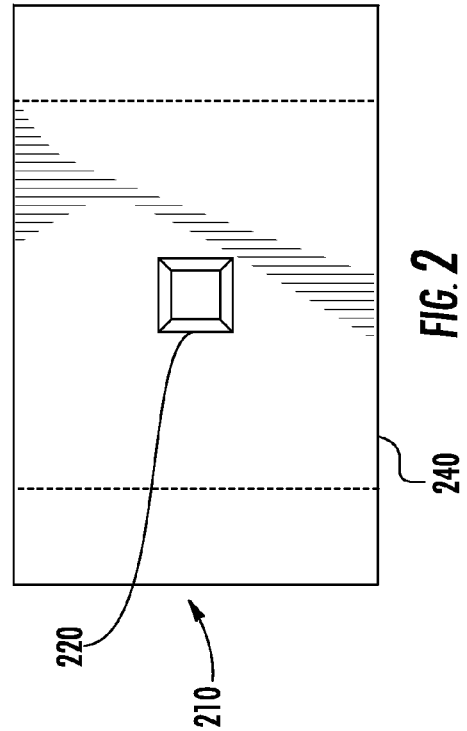

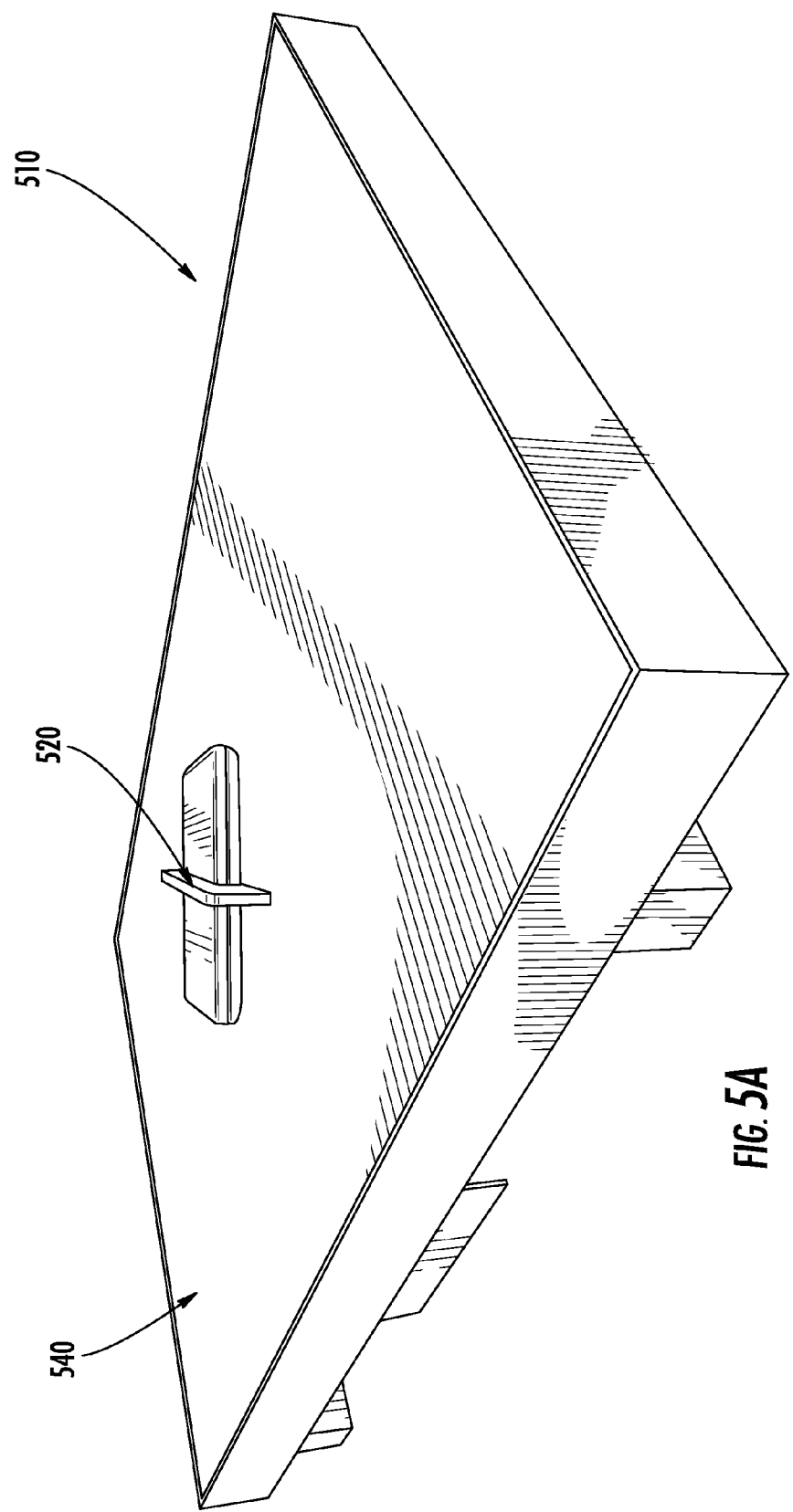

SELF-ALIGNING TEST WEIGHT

CROSS-REFERENCE TO RELATED APPLICATIONS

This application claims priority to and the benefit of the filing date of U.S. Provisional Application No. 61/658,216, filed Jun. 11, 2012, the disclosure of which is hereby incorporated by reference herein in its entirety.

BACKGROUND OF THE INVENTION

1. Field of the Invention

The present invention relates to test weights for testing the load capacity of a crane. More specifically, the present invention provides a novel system and approach for the simple and efficient load testing for a crane using solid weights.

2. Description of Related Art

Cranes are an essential component of nearly all commercial construction operations. To ensure the safety of personnel and resources at such operations, the load capacity of a crane must be pre-tested to verify that the crane is capable of lifting a particular load. Conventional methods for testing the load of a crane use a variety of weight designs and systems ranging from water weight bags to weighted platforms. In these other systems, a separate platform is required for the weights to be place upon before the crane is able to lift the system and be weight tested. With the addition of a platform component to the system, the challenge of securing the weights in place for stacking and movement of the platform is then required. Additionally, other systems require pins and hooks that a lifting device can attach a cable to in order to move the test weights into their stacked position on the platform. Finally, the required platform utilized by other systems created an overall unit that requires a greater amount of space which creates a storage issue as well as a safety issue. However all of these systems often require significant time and effort to configure a proper weight to test the crane load capacity.

One existing approach is disclosed in U.S. Pat. No. 6,725,730 entitled "Crane Test Weight Assembly and Method." This approach uses a holder apparatus comprised of a platform with a pole or post oriented perpendicular to the platform. The weights have a centrally located hole, shaped to fit the pole or post. The weights additionally have a pair of lifting eyes disposed on exact opposite sides of the periphery of the weight. The eyes are in line with each other and this line can intersect the central axis of the opening on the weight used for placement on the post. After selecting the desired weight or plurality of weights, the weights are individually lifted and stacked into place onto the post and platform using lifting eyes and shackles or other selected rigging. Once the weights have been successfully lowered and aligned onto the platform, the crane then lifts the holder apparatus for weight testing. The system disclosed in this patent offers a method for selecting the desired amount of weight, but safety precautions demand that the weights must still be lowered onto a platform before the holder apparatus with the weights can be lifted by the crane.

Another existing approach is disclosed in U.S. Pat. No. 6,578,441 entitled "Crane Testing Apparatus and Associated Load Testing Method." This system also uses an apparatus upon which the weights can be stacked. The weights used in this system comprise tabs on the top of the weight and holding pin openings in the bottom of the weight through which the test weight may be retained on the base of the frame. However the method for stacking the weights onto the apparatus relies upon four vertical frame posts and two intermediate beams that are used to secure the weights to the apparatus. The heavier weights are stacked on the base frame between the frame posts while the light load weights are stacked on the other sides of such frame posts. The heavier weights contain tabs on the top and holding pin openings on the bottom to secure the weights to the base frame. The lighter weights must be secured to the base frame using tie-down straps attached at their upper ends to the intermediate lift beams and at their lower ends anchored by clips to the ends of the base frame. However, this system still requires that the weights be loaded onto the base frame or platform, thereby requiring additional steps to load and align the weights on the platform and secure the plurality of weights to the platform. These additional steps require additional time and effort of the assigned personnel. Thus, a system is preferred that can eliminate these additional loading steps and maximize efficiency, while providing comparable levels of system reliability, durability, and safety.

SUMMARY OF THE INVENTION

A novel system for testing the load capacity of a crane is presented herein. The test weights are configured to provide weights in any size. Preferable are test weights in any weight ranging from 100-35,000 lbs. which can best be embodied through the use of multiple categories of test weights. Preferably, the test weights are provided in a variety of weight categories ranging from 100-35,000 lbs. The categories would allow for a wide variety of stacking configurations to create the final test weight by offering weights at 100-250 lbs., 200-400 lbs., 500-750 lbs., 1,000-1,500 lbs., 2,000-4,000 lbs., 5,000-7,500 lbs., 10,000-15,000 lbs., 17,500-25,000 lbs. and 25,000-35,000 lbs.

The weights can be provided individually, however, the advantages of the weights are best realized in a test weight system comprising at least two stackable test weights. Preferably, the system is configured to provide a plurality of test weights, composed of between 2 and 10 test weights from the various categories, where the system provides the weights stacked in about half the space of other test weight systems, which simultaneously provides both safety and storage advantages.

The test weights comprise a solid material, such as solid steel however, the test weights can be comprised of other materials such as concrete, wood or a composite material, or can be hollow and filled with a material such as sand, water, or molten metal. The test weights can be referred to as plates, blocks or slabs when referring to the system as a whole or the individual upper and lower portions that combine to form one test weight unit.

Each weight in the system comprises a void in the bottom face of the weight. Although the void is shown in the center of the weight, the void can be disposed at any location on the lower exterior surface of the weight, or several voids can be used at various desired locations on the weight, such as near each of the four corners of the weight. On top of the weight is disposed a block, here after referred to as a block lock, disposed directly above the void in the bottom of the weight and configured of a shape and size to be received by the void in the bottom of another weight stacked on top of the weight. Each weight can comprise any number of voids and any corresponding number of block locks. Indeed, systems can even comprise weights with differing numbers of voids and/or block locks.

The block lock in preferred embodiments is centrally disposed on the upper surface of the weight. It is shaped to facilitate alignment of a corresponding void on another weight. The block lock can have a base that is just slightly smaller in perimeter than the corresponding void. Preferably, the block lock is pyramidal in shape however the block lock can be of a cubic, rectangular, cylindrical or of a semi-spherical configuration. The void in the weight plate is configured to allow for the block lock disposed on the surface of one weight to be received by the void in the lower exterior surface of a second weight. The void should be of such configuration that the shape is the same as the block lock but slightly larger in perimeter to accommodate the block lock. Alternatively, the block lock and corresponding voids can be of different shapes, so long as they are sized such that the block lock of one weight is received by the void of another weight and retained therein. This configuration allows for a weight to be lowered onto another weight using a forklift and the void in the weight being lowered to self-align with the block lock on the weight below.

In preferred embodiments, the block lock is hollow and can be filled with metal material. The block lock can be any size, but is preferably sized to allow for filling with metal (such as lead) to add up to 400 lbs. to the weight. In this manner, the weights can be provided with a precision preferably within about 100 lbs. of the target mass for that weight.

In embodiments, the test weight comprises at least one gap between the upper exterior surface of one weight and the lower exterior surface of another weight. The gap in preferred embodiments is shaped to facilitate the positioning of a lifting device, such as the two parallel beams of a forklift or straps outfitted to a hook in a crane, to lift and stack the test weights on top of one another without the use of additional pins or hooks, or to lift one or more test weights to perform a test for a crane.

Specific objects of the invention include Object 1, which is a test weight system for testing load capacity of a crane, the system comprising: i) a plurality of stackable test weights, each test weight comprising: a planar material; at least one void disposed in or on a bottom surface of the test weight; at least one protrusion disposed on the top of the test weight, wherein the protrusion is operably configured to be received by the void of another test weight in a manner that provides for self-aligning of the weights when stacked; ii) at least one gap disposed between test weights when stacked.

Object 2 is the test weight system of Object 1, wherein one or more of the test weights comprises rounded edges.

Object 3 is the test weight system of Object 1 or 2, wherein the at least one void is a recess and not a pass-through void.

Object 4 is the test weight system of any of Objects 1-3, wherein the planar material is steel, wood, plastic, glass, cement, metal, or any combination or composite thereof.

Object 5 is the test weight system of any of Objects 1-4, wherein the planar material is a hollow box.

Object 6 is the test weight system any of Objects 1-5, wherein the planar material is a solid slab of metal.

Object 7 is the test weight system of any of Objects 1-6, wherein the planar material is steel or iron.

Object 8 is the test weight system of any of Objects 1-7, wherein the planar material is lead.

Object 9 is the test weight system of any of Objects 1-8, wherein the slab of metal comprises elongated feet disposed on the bottom surface of the test weight on both sides of the void.

Object 10 is the test weight system of any of Objects 1-9, wherein the elongated feet are hollow.

Object 11 is the test weight system of any of Objects 1-10, wherein the elongated feet comprise weighted material disposed in the hollow feet.

Object 12 is the test weight system of any of Objects 1-11, wherein no additional member is included to align the plurality of test weights.

Object 13 is the test weight system of any of Objects 1-12, wherein the protrusion is a cross shaped protrusion.

Object 14 is the system of any of Objects 1-13, wherein the protrusions and voids are different shapes.

Object 15 is a test weight comprising: a solid slab of metal; at least one protrusion disposed on a top surface of the slab; at least one receptacle disposed on a bottom surface of the slab; two or more elongated hollow feet disposed on the bottom surface of the slab and on both sides of the receptacle, wherein the feet are operably configured to provide for a gap between slabs when stacked; wherein the protrusion is operably configured to be received by the receptacle of another test weight in a manner that provides for self-aligning of the weights when stacked.

Object 16 is the test weight of Object 15 or the system of any of Objects 1-14 comprising one or more test weight of Object 16, wherein the slab and feet are welded to form a single unit.

Object 17 is the test weight of Object 15 or 16, or the system of any of Objects 1-14 comprising one or more test weight of Object 17, comprising forklift guides.

Object 18 is a method of testing load capacity of a crane comprising: supplying a plurality of stackable test weights with a gap between the weights; lifting one or more of the plurality of test weights a suitable distance for a time that allows inspection of the crane for deformation of parts or slippage.

Object 19 is the method of Object 18, wherein the plurality of test weights are operably configured for interlocking with one another.

Object 20 is the method of Object 18 or 19, wherein each test weight comprises: a solid slab of metal; at least one protrusion disposed on a top surface of the slab; at least one receptacle disposed on a bottom surface of the slab; two or more elongated hollow feet disposed on the bottom surface of the slab and on both sides of the receptacle, wherein the feet are operably configured to provide for a gap between slabs when stacked; wherein the protrusion is operably configured to be received by the receptacle of another test weight in a manner that provides for self-aligning of the weights when stacked.

BRIEF DESCRIPTION OF THE DRAWINGS

The accompanying drawings illustrate certain aspects of some embodiments of the present invention, and should not be used to limit or define the invention. Together with the written description the drawings serve to explain certain principles of the invention.

FIG. 1 is a schematic diagram showing a side elevation view of a single self-aligning test weight embodiment of the invention.

FIG. 2 is a schematic diagram showing a top view of a self-aligning test weight embodiment of the invention.

FIG. 3 is a schematic diagram showing a side elevation view of a plurality of self-aligning test weights in a stacked configuration according to an embodiment of the invention.

FIGS. 5A-B are schematic diagrams of a test weight with flat edges according to an embodiment of the invention.

DETAILED DESCRIPTION OF VARIOUS EMBODIMENTS OF THE INVENTION

Figure 4A:
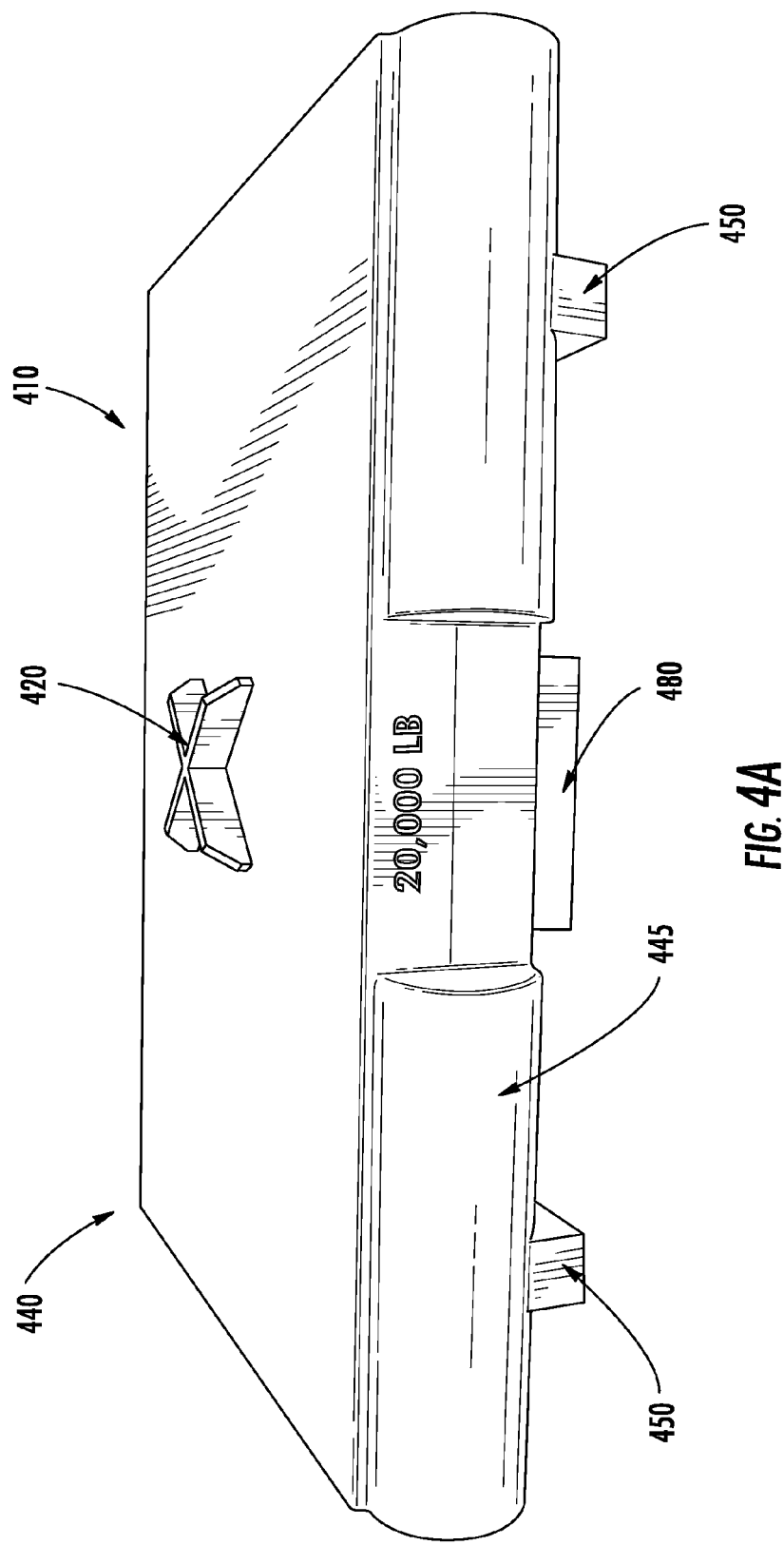
FIGS. 4A-B are schematic diagrams of a test weight with rounded edges according to an embodiment of the invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

As shown in FIG. 1, embodiments of the invention provide test weight units 110 configured so that the weights are capable of self-alignment with other weights when stacked. For example, as illustrated, to enable the self-alignment feature of the weights, test weight 110 can comprise a protrusion on the upper surface of the weight, otherwise referred to as a block lock 120. The block lock 120 in embodiments is centrally disposed on the upper surface of the test weight unit 110, as shown in FIG. 1. It is shaped to facilitate alignment of a corresponding void on another test weight unit 130. As shown, the block lock 120 can have a base that is just slightly smaller in area than the corresponding void 130. In embodiments, the void 130 is a square which can accept the corresponding block lock 120 and lock into any weight 110 in the same set, created via precision water jet cut, molding or carving.

In embodiments, the test weight can be formed by welding together two weights, such as an upper slab 140 and a lower slab 150, or an upper slab and feet. By shaping or sizing the upper and lower slabs differently, a gap 60 can be created when the test weights are stacked. The size of this gap is dependent upon the relative dimensions of the length or the width of the lower and upper slabs but in embodiments is large enough to accommodate a lifting device 70 (such as a forklift, lifting bars, or a sling) for transport of a weight unit 110.

Figure 9:
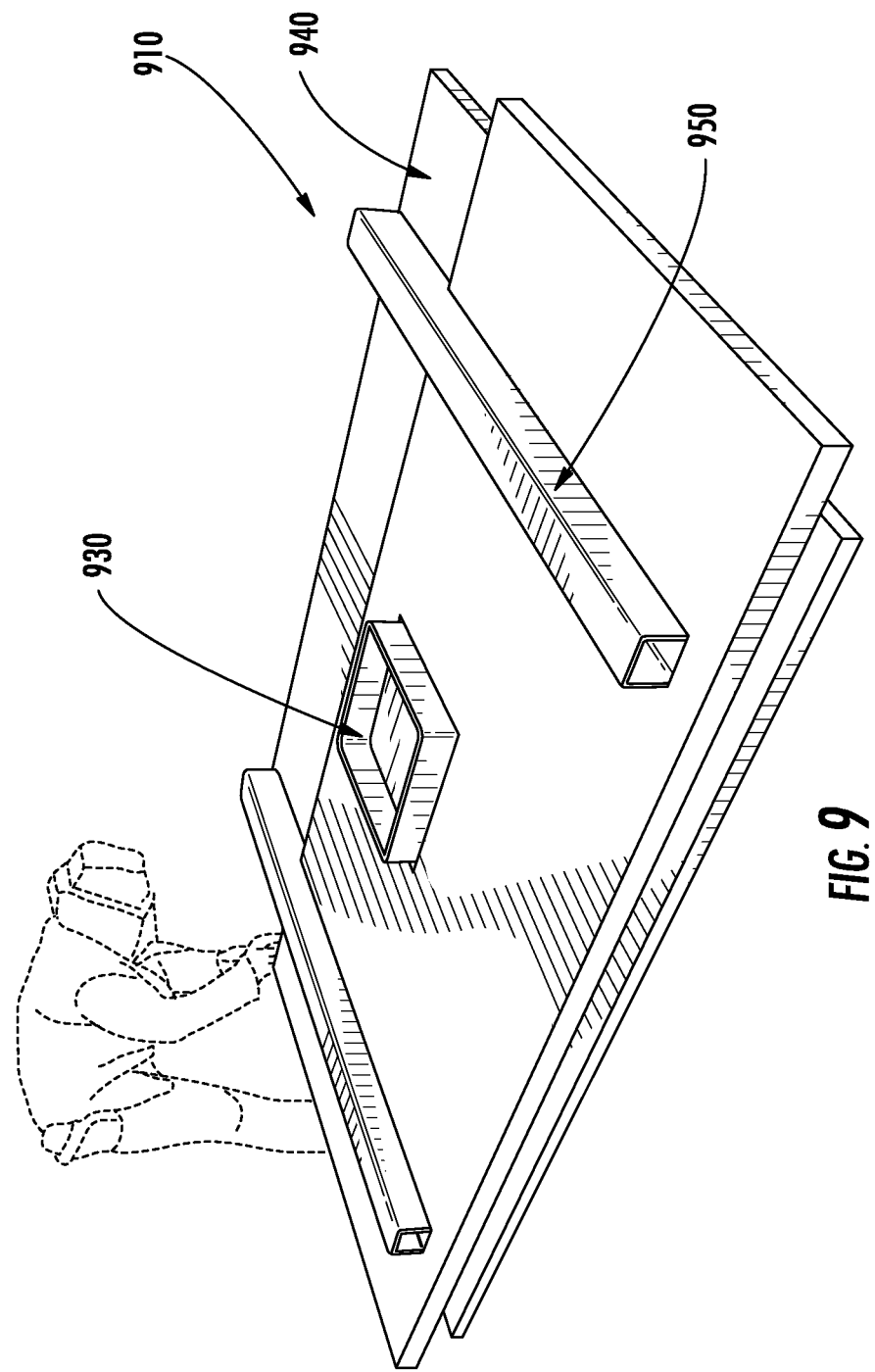
FIG. 9 is a schematic diagram showing a method of making a test weight by attaching various components to the underside of the upper exterior surface.

As shown in FIG. 2, the top of the block lock 220 can be cross-shaped, pyramidal, cubic, cylindrical, or semi-spherical in shape. In embodiments, the block lock 220 is hollow and can be filled with metal material. The block lock 220 can be any size, and disposed on the upper slab 240 of the test weight 210. In embodiments, the locking mechanism is shaped and sized to allow for filling with metal or another material, such as lead, iron, sand, water, etc., to add up to about 400 lbs. to the weight. The fill material can be a liquid, molten material, particles, or solid bars. In this manner, the test weight units 210 can be provided with precision preferably within about 100 lbs. of the target mass for a particular weight unit 210. In preferred embodiments, the test weights can comprise feet, such as 4" box tubing, which can be filled with material to adjust the finished weight of the test weight, as shown in FIG. 9. One or more solid steel bars, for example, can be inserted into the box tubing to achieve the desired weight. The box tubing type feet can be disposed on the bottom surface of the test weight and can provide for several additional functions, including as supports for the weights and as spacers to provide for a desired spacing between blocks. The feet thus can be any size and can be any shape, including rectangular, and can have a diameter ranging from 1 inch, 2 inches, 3 inches, 4 inches, 5 inches, 6 inches, 7 inches, 8 inches, etc.

As shown in FIG. 1 and FIG. 3, the length of the upper slab 140, 340 can be greater than the length of the lower slab 150 to facilitate the transport of the weight unit 110, 310 for stacking on top of another weight unit. Alternate embodiments can have the length of the upper slab 140, 340 equal that of the lower slab 150, 350 while the width of the upper slab 140, 340 can be greater than the width of the lower slab 150, 350 to facilitate the transport. The length of the lower slab 150, 350 can be between 10%-90% of the length of the upper slab 140, 340 such as about 15-80%, or about 20-75%, or about 30-60%, or about 45-50%. Preferably, the feet are about 80-100% the length of the slab, such as from 85-95%, or about 90-98%, or 96-99%, while the width of the feet is about 2-40% of the width of the slab, such as about 5-35%, or from about 10-30%, or from 15-25%, or about 20%. The same relative dimensions can be applied to the width of the two slabs when the length of the two slabs is the same. The relative difference in embodiments is large enough to facilitate the placement of a lifting device 70 for the transport of the weight unit 110, 310, onto or to create a plurality of weight units 110, 310 that create the test weight system 300. As shown, the lifting device 70 can be inserted into the space or gap 60 between stacked test weights, which space 60 is available due to the specific configuration of the test weights.

The present system 300 is intended for use in crane load weight testing. The testing is accomplished by selecting the desired test weight through the combination of various weight plates 310, and stacking them using a lift device 70 as shown in FIG. 3. At this point, the lifting device 70 is placed in the gapped space 60 present in the weight plate 310 at the bottom of the plurality of weight plates 310 to be lifted. Any number of test weights 310 can be lifted off and away from the system 300. For example, as shown in FIG. 3, all of the test weights except for the bottom most test weight in the stack are lifted. Once the lifting device is in place, the crane then lifts the system 300 a suitable distance from the ground to allow personnel to inspect the crane for several minutes looking for deformation of parts or slippage of the crane under the load.

As further shown in FIG. 3, embodiments of the self-aligning test weight systems 300 according to the invention can comprise a plurality of solid test weight units 110. The system can be effective as a single test weight 310 or as a plurality of weights 300. The test weight system 300 is designed such that optimally, a combination of two or more weights 310 is stacked and a desired load weight may be selected quickly by using a combination of weights from the various available weight categories ranging from 100-35,000 lbs. Any weight can be used for the test weights, including from 100, 200, 250, 300, 350, 400, 450, 500, 550, 600, 650, 700, 750, 800, 850, 900, 1,000, 1,500, 2,000, 2,500, 3,000, 3,500, 4,000, 4,500, 4,600, 4,700, 4,800, 4,900, 5,000, 5,500, 6,000, 6,500, 7,000, 7,500, 8,000, 9,000, 10,000, 12,000, 15,000, 20,000, 22,000, 25,000, 30,000, or 35,000 to name a few.

As shown in FIGS. 4-11, the locking mechanism for the test weights (otherwise referred to as the block lock) can preferably be in the form of a cross lock and cross lock receiver. More specifically, protrusions in the form of a cross can be disposed on one surface of the test weight, such as the upper surface. A corresponding protrusion on the bottom surface of the test weight can be shaped and sized to receive the cross shaped protrusion disposed on the top surface of another test weight. With such a configuration, when a test weight is lowered onto another test weight, the weights will automatically align so that the cross lock of one test weight will be received by the cross lock receiver of another test weight in a particular desired orientation.

Figure 4B:
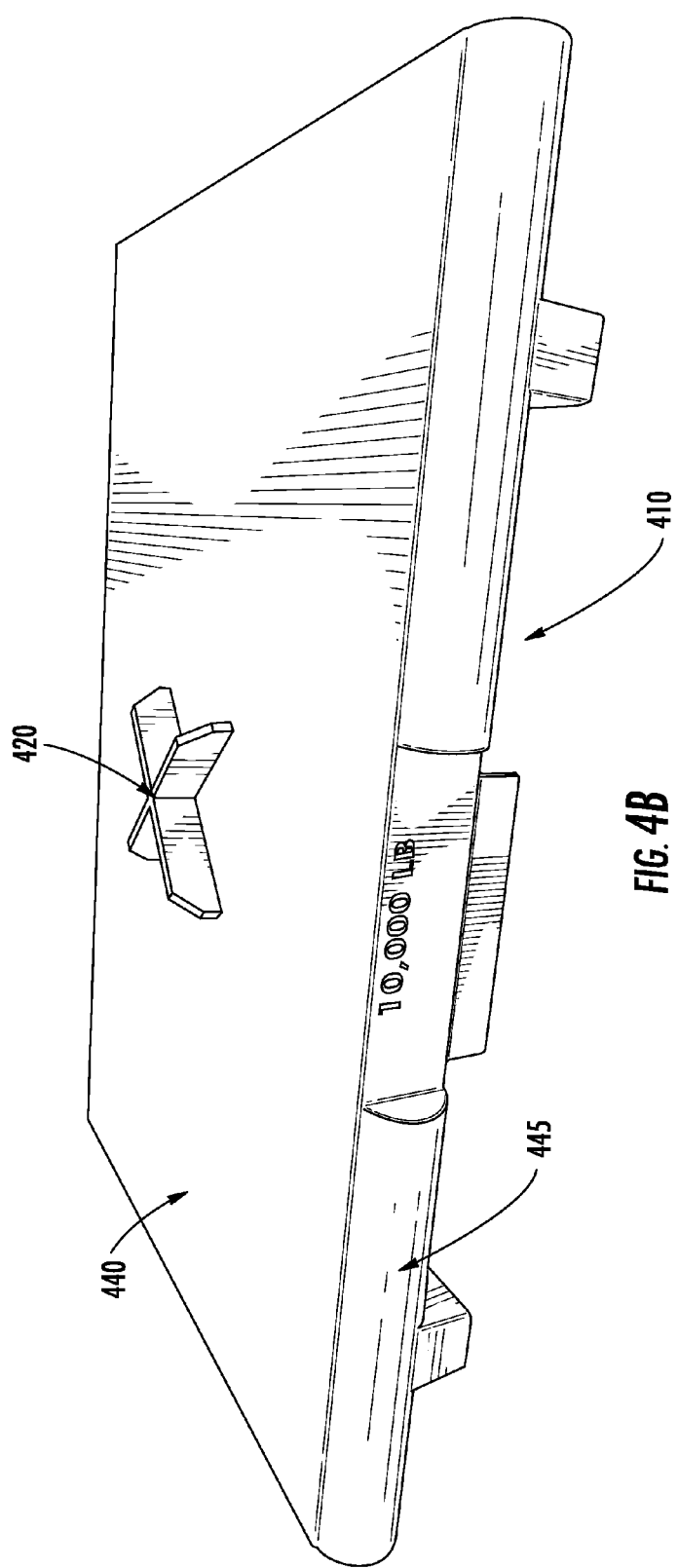
Figure 5B:
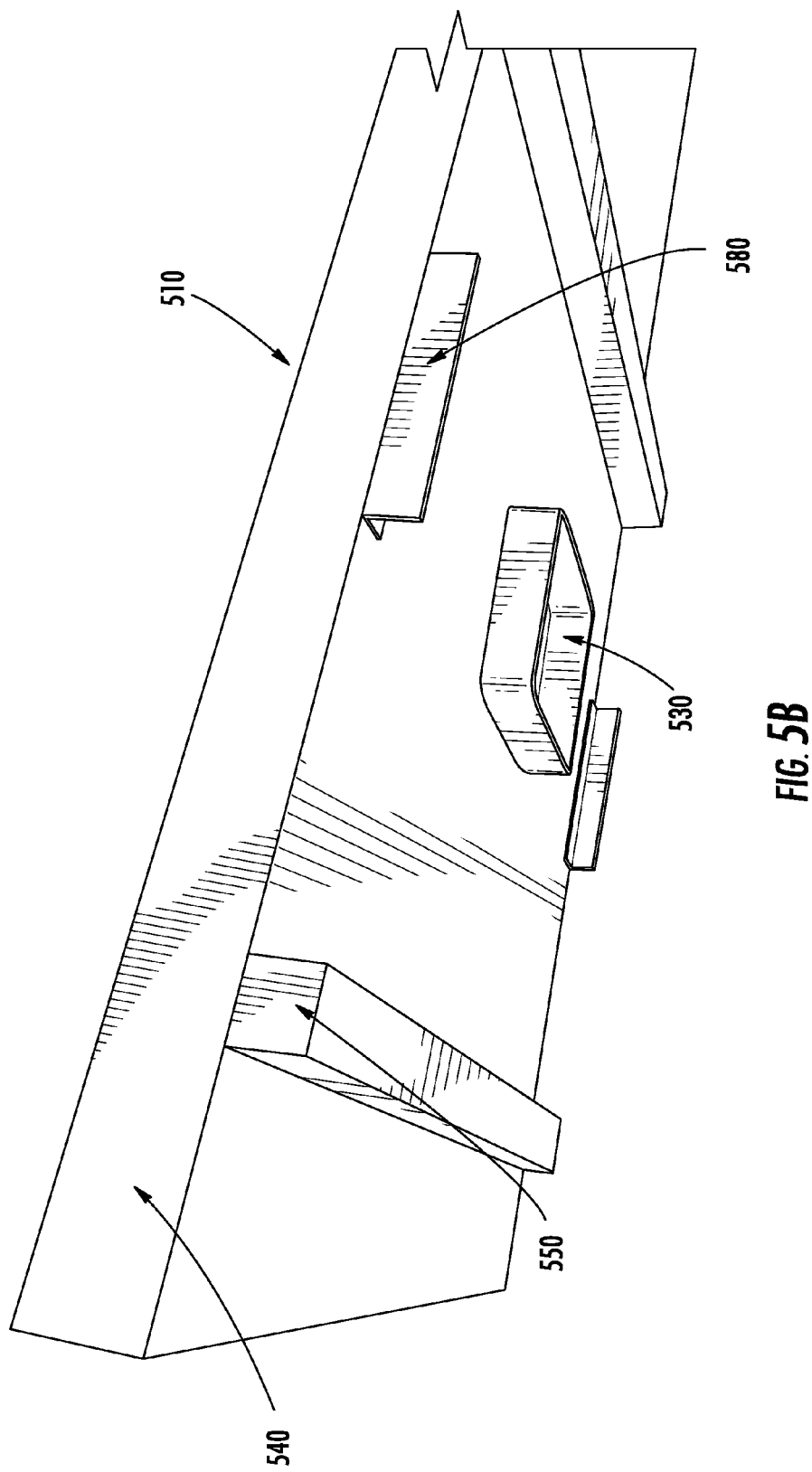

The embodiment of a single weight unit 410, as shown in FIGS. 4A-B, can additionally be created through the use of a form or mold thus creating one solid piece. The block lock or cross lock, 420, can also be configured so as to be an integral member of the weight unit through a molding process to create one solid, seamless unit.

In embodiments, and as shown in FIGS. 4A-B, the test weights 410 can comprise edges with heavy wall pipe 445 welded to the side of the weight, typically to the side of the upper slab 440, so that nylon slings can basket the weight instead of using lifting bars. In embodiments of the invention, the nylon slings aid in lifting the test weight by passing underneath and around the upper slab 440 and are held in place, or guided, by lower slab 450 and flange 480 connected to the upper slab 440. Alternatively, the test weights can be molded with this configuration. More specifically, nylon slings are the preferred mechanism for lifting the test weights, however, the combination of heavy loads of test weights having square edges tends to weaken or even cut nylon straps during the lifting process, which can lead to catastrophic failure. The rounded edges 445 of the test weights in embodiments can also be hollow to allow for filling with additional weighted material to achieve a particular desired weight for the test weight. Test weights may also comprise non-rounded edges, such as flat edges, as those shown in FIGS. 5A-5B. As the components of the test weights 410, 510 are similar, aside from the rounded edges, the rounded and flat edge test weights may be used together or interchangeably, depending on the lifting device. The block lock, or cross lock, 420 shown in FIG. 4 is approximately the same size as the cross lock 520 shown in FIG. 5 and therefore the cross lock 420 of the embodiment shown in FIG. 4 may communicate with the cross lock receiver, or void, 530 of the test weight 510 shown in FIG. 5. The void 530 is located on the underside of the upper slab 540, in addition to the lower slab 550 and flanges 580. In preferred embodiments the void 530 is between two sides of the lower slab 550 and is centered on the upper slab 540, in line with the flange or flanges 580. This location of the void or cross lock receiver allows for use of a plurality of lifting devices and provides even weight distribution when the test weights 510 are stacked.

Figure 6:
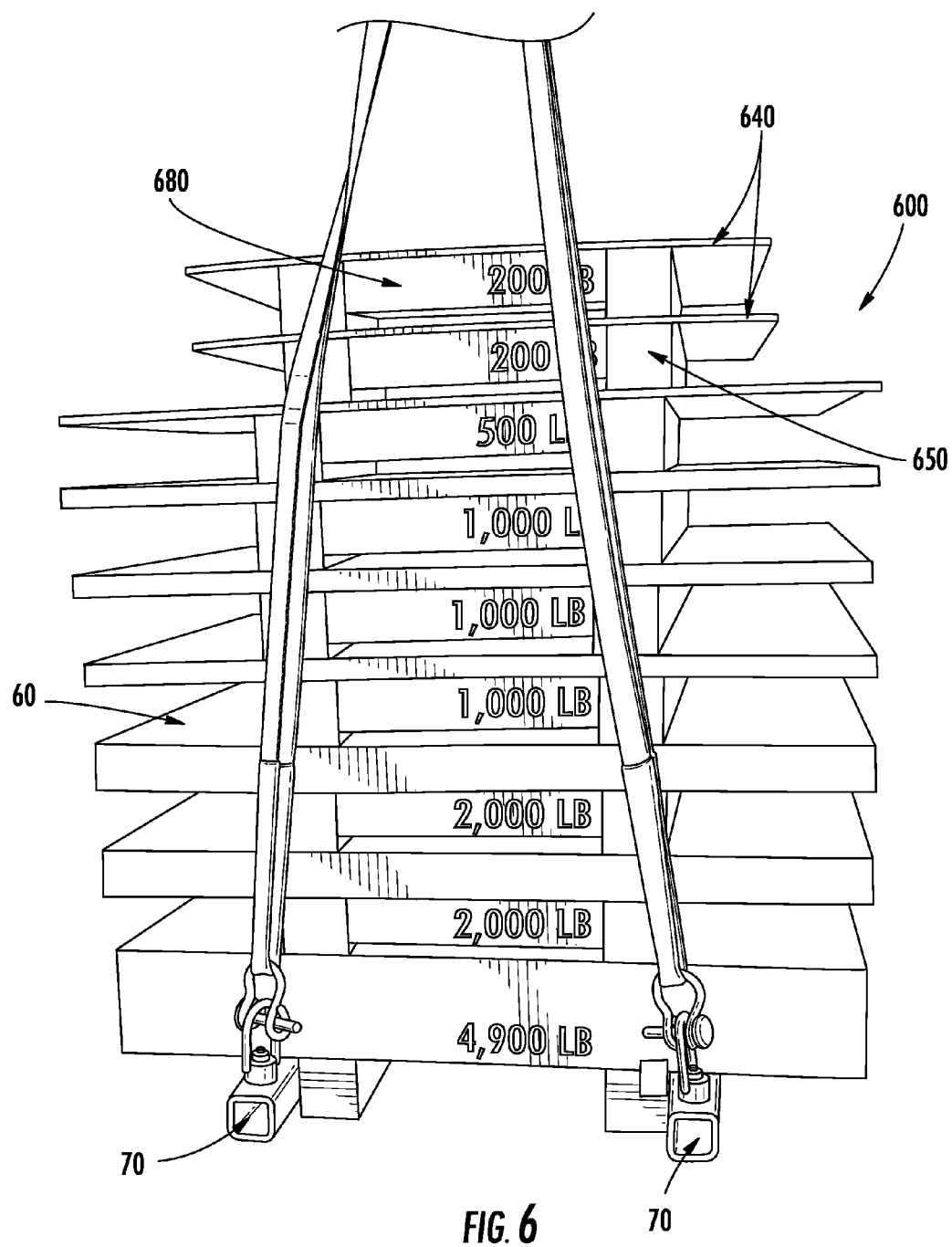
FIG. 6 is a schematic diagram showing a test weight system of the invention comprising a plurality of test weights of a plurality of sizes.

The figures further show how the test weights 610 can be stacked as a system 600, as shown in FIG. 6. In preferred embodiments, the test weights are stacked with the lower slab 650 of one test weight resting on the upper slab 640 of a different test weight beneath it, and where preferably the heavier test weights are provided at the bottom of the stack which allows for lifting of one or more of the test weights at any portion of the stack. In embodiments, instead of using a sling to lift the weights, lifting bars 70 can be used to pick up all the weights or any portion of the weight stack 600. The lifting bars 70 or slings are inserted into the space left between two weights when stacked. In embodiments, the test weights can also comprise one or more side flanges 680 disposed on the underside of the weight, which can serve as an indicator of the weight of the test weight 610 and as a guide for lifting one or more of the test weights from the stack 600. When used as a guide, the flange 680 can be the same width as the cross lock receptacle, such that when a forklift is inserted between weights the forklift operator will be prevented from accidentally running into the receptacle even though the receptacle may not be visible to the operator, since the flange 680 disposed on the outer edge of the weight is visible.

Figure 7:
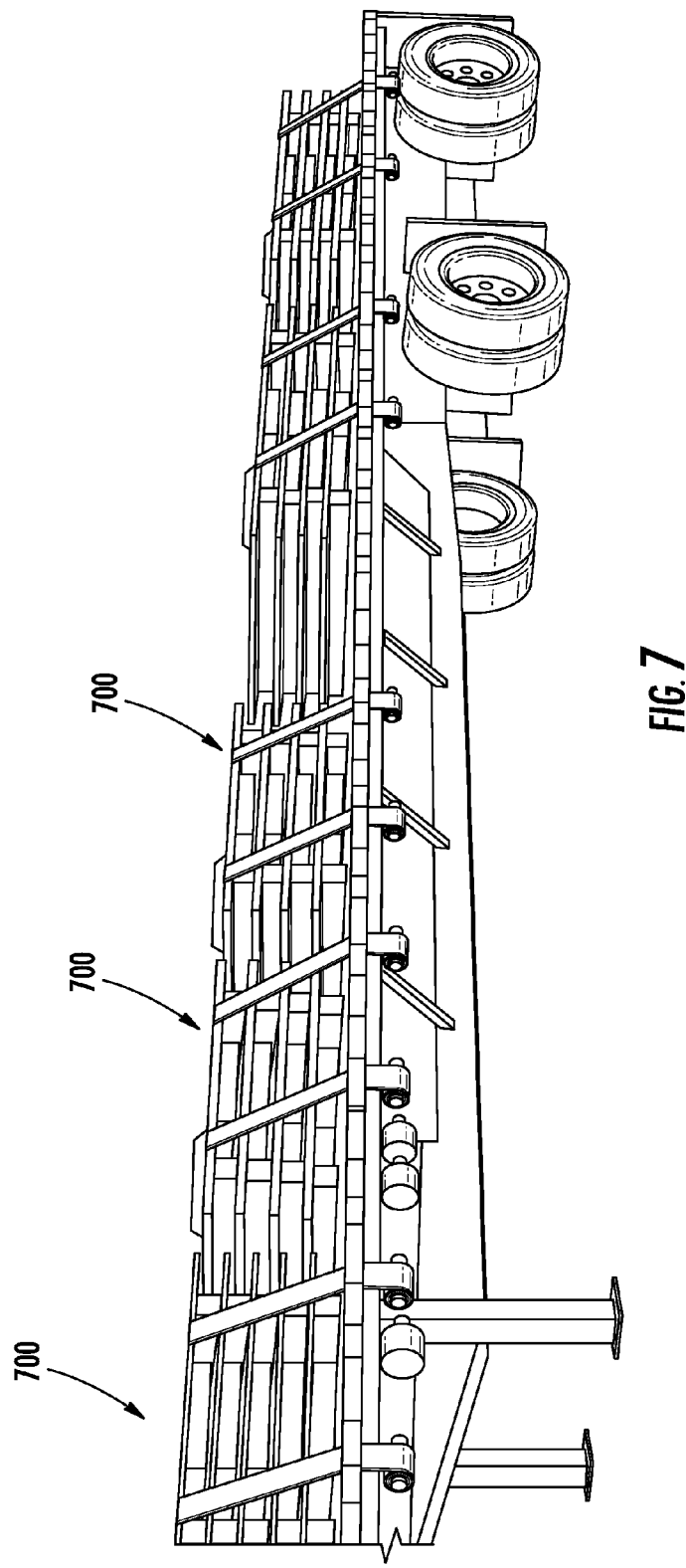
FIG. 7 is a schematic diagram showing a plurality of test weight system according to embodiments of the invention.
Figure 8:
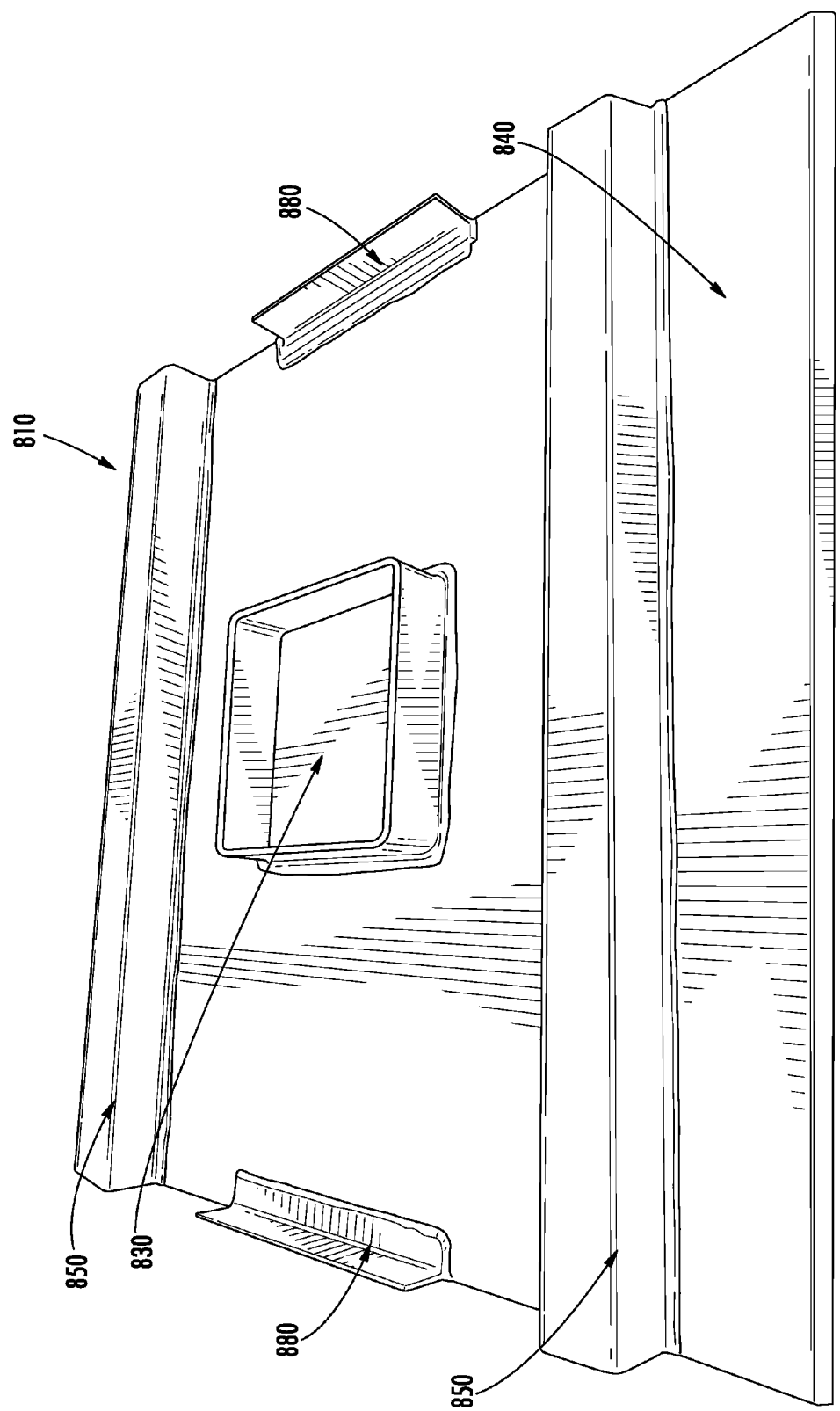
FIG. 8 is a schematic diagram showing a perspective view of a test weight of the invention illustrating the underside of the upper exterior surface.

Successful operation of the system requires a lifting device of two parallel beams, such as a fork lift or a sling. The parallel beams or straps of the sling of the lifting device fit into the gap 60 on the bottom of each weight unit 610 to lift each unit into place on top of the stack of test weights 600. In one embodiment, the loading end of the lifting cable of the crane has a lifting device 70. Personnel on the ground can quickly secure the lifting device 70 to select the desired weight. A higher desired weight implies that more weight units 510 should be lifted, hence the lifting device 70 should be secured closer to the bottom of the weight stack. In a second embodiment, a forklift having a lifting device 70 can be used to transport the plurality of test weights as weight stacks 600, 700, or a plurality of weight stacks, to a desired location, as shown in FIG. 7.

In embodiments, the lower exterior surface 850 of one or more test weights 810 can comprise a void 830, also referred to as a block lock, or cross lock, or receiver, shaped in a manner that it may receive the block lock, or cross lock, as shown in FIG. 5A (520) of the weight unit 810 directly beneath the surmounted weight unit 810. The void 830 can be formed within the upper slab 840, or can be formed by additional material disposed on the lower surface of the upper slab 840. This configuration allows for a test weight unit 810 to be lowered onto another weight unit 810 using a lifting device comprising two parallel beams 70, as shown in FIG. 3. Void 830 in the test weight unit 810 being lowered causes the test weight unit 810 to self-align with the block lock of the test weight unit 810 on the top of the stack. The self-alignment is achieved through the configuration of the block lock and the corresponding void and can additionally be aided by the flange or flanges 880, located at the edge of the test weight 810. In embodiments, void 830 is designed to be just slightly larger in perimeter than the block lock, creating a tight fit between the protrusion and receiver that leads to self-alignment once the void has been lowered onto the block lock. Other configurations for the block lock are possible, such as any square or rectangular type block or even a semi-spherical type block, or preferably a cross type protrusion. The void 830 and the block lock do not need to be the same shape the configuration just has to be such that the block lock is able to fit into the void 830 of the weight unit 810 above it. Similarly, the void 830 can be configured in a way that the void is not lock tight to the block lock.

FIG. 9 shows a method of making a test weight 910 using a jig. The jig comprises cutouts for placement of a lower exterior surface 950, such as for box tubing, and a receiving void 930 (to receive a block lock/cross lock of another test weight when stacked). The jig is aligned on the underside of the upper exterior surface 940 of the test weight and the box tubing 950, and cross lock receiver 930 are aligned within the jig. Once the lower exterior components are secured in place, such as by welding as shown, the jig is removed.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. It is intended that the specification and examples be considered as exemplary in nature and that variations that do not depart from the essence of the invention are intended to be within the scope of the invention. Further, the references cited in this disclosure are incorporated by reference herein in their entireties.

The invention claimed is:

1. A test weight system for testing load capacity of a crane, the system comprising:
   i) a plurality of stackable test weights, each test weight comprising:
      a planar material;
      at least one void disposed in or on a bottom surface of the test weight;
      at least one protrusion disposed on the top of the test weight, wherein the protrusion is operably configured to be received by the void of another test weight in a manner that provides for self-aligning of the weights when stacked;
      at least one support structure disposed on a different surface of the test weight than the at least one protrusion and which different surface is the bottom surface of the test weight;
   ii) at least one gap disposed below the bottommost test weight and disposed between test weights when stacked.

2. The test weight system of claim 1, wherein one or more of the test weights comprises rounded edges.

3. The test weight system of claim 1, wherein the at least one void is a recess and not a pass-through void.

4. The test weight system of claim 1, wherein the planar material is steel, wood, plastic, glass, cement, metal, or any combination or composite thereof.

5. The test weight system of claim 1, wherein the planar material is a hollow box.

6. The test weight system of claim 1, wherein the planar material is a solid slab of metal.

7. The test weight system of claim 6, wherein the planar material is steel.

8. The test weight system of claim 6, wherein the planar material is lead.

9. The test weight system of claim 6, wherein the slab of metal comprises the at least one support structure in the form of elongated feet attached to the slab of metal along the longer side of the elongated feet.

10. The test weight system of claim 9, wherein the elongated feet are hollow.

11. The test weight system of claim 10, wherein the elongated feet comprise weighted material disposed in the hollow feet.

12. The test weight system of claim 1, wherein no additional member is included to align the plurality of test weights.

13. The test weight system of claim 1, wherein the protrusion is a cross shaped protrusion.

14. The system of claim 1, wherein the protrusions and voids are different shapes.

15. A test weight system for testing load capacity of a crane, the system comprising:
   i) a plurality of stackable test weights, each test weight comprising:
      a planar material;
      at least one void disposed in or on a bottom surface of the test weight;
      a single protrusion centrally disposed on the top of the test weight
      wherein either the protrusion or the at least one void is square; and
      wherein the protrusion is operably configured to be received by the void of another test weight in a manner that provides for lateral self-aligning and interlocking of the weights when stacked;
      and
   ii) at least one gap disposed between test weights when stacked.

16. The test weight system of claim 15, wherein the planar material comprises elongated feet disposed on the bottom surface of the planar material and attached to the planar material along the longer side of the elongated feet.

17. The test weight system of claim 16, wherein the elongated feet are hollow.

18. The test weight system of claim 16, wherein the elongated feet are hollow and comprise box tubing.

19. The test weight system of claim 17, wherein the elongated feet comprise weighted material disposed in the hollow feet.

20. The test weight system of claim 17, wherein the elongated feet have a length that is 80-100% of the length of the planar material.

* * * * *